United States Patent [19]

Federman

[11] Patent Number: 5,200,430
[45] Date of Patent: Apr. 6, 1993

[54] DEBRIDEMENT OF BODILY CAVITIES USING DEBRIDEMENT FLUIDS

[75] Inventor: Jay L. Federman, Philadelphia, Pa.

[73] Assignee: Escalon Ophthalmics, Inc., Skillman, N.J.

[21] Appl. No.: 672,972

[22] Filed: Mar. 21, 1991

[51] Int. Cl.$^5$ .............................................. A61K 47/00
[52] U.S. Cl. ......................................... 514/772; 424/5
[58] Field of Search .............................. 424/5; 514/772

[56] References Cited

U.S. PATENT DOCUMENTS 4,490,351  12/1984  Clark, Jr. ................................. 424/5

OTHER PUBLICATIONS

Nabih, M., et al., "Experimental Evaluation of Perfluorophenanthrene as a High Specific Gravity Vitreous Substitute: A Preliminary Report," *Ophthalmic Surgery*, 20(4):286–93 (1989).

Chang, S., et al., "Experimental Vitreous Replacement With Perfluorotributylamine," *Am. J. Ophth.*, 103:29–37 (1987).

*Primary Examiner*—Frederick E. Waddell
*Assistant Examiner*—Zohreh A. Fay
*Attorney, Agent, or Firm*—Panitch Schwarze Jacobs & Nadel

[57] ABSTRACT

Foreign substances may be removed from a mammalian body cavity containing an aqueous phase by injecting into the cavity a water-immiscible, optically clear, biocompatible debridement fluid to at least partially displace the aqueous phase, and removing the aqueous phase and the foreign substances. In addition, a method is provided for visualizing a transparent foreign substance in a mammalian body cavity using a water-immiscible, optically clear, biocompatible fluid having a refractive index different from that of water. The debridement fluid may also be used to reposition desirable substances, such as a lens in an ocular cavity, or to remove a secondary membrane from a cavity lining or structure. Preferably, a liquid heavier than water, such as a perfluorocarbon liquid, is used as the debridement fluid.

19 Claims, 3 Drawing Sheets

DEBRIDEMENT OF BODILY CAVITIES USING DEBRIDEMENT FLUIDS

FIELD OF THE INVENTION

The present invention relates to methods for the debridement of enclosed body cavity spaces which must remain substantially free of foreign substances to function properly. More particularly, the invention is directed to removal of foreign substances from the eye.

BACKGROUND OF THE INVENTION

Within the mammalian body are many cavities. These include organ cavities and tissue cavities within which one or more organs are located. Depending on the particular cavity, these cavities are lined by endothelial cells, epithelial cells and/or basilamina material, which is produced by cellular foot plate secretions. Such tissue and organ cavities include the abdominal cavity, thoracic cavity, fallopian tube, uterine cavity, intraocular cavity, joint space or intra-articular cavity, central nervous system ventricular cavity and the dural spaces. Despite different functions, all cavities share the common requirement that they must be kept clean of foreign substances to maintain normal function.

As used in this disclosure, the term "foreign substances" is not limited to debris and fluid from outside the body but will be recognized in its broadest sense by those skilled in the medical arts to include foreign cells, which include mal- or dysfunctioning or displaced indigenous cells, proteins, sera, inflammatory cells, blood cells, tumor cells, tissue debris, infectious organisms (i.e., bacteria, virus and fungi) in addition to foreign bodies, such as glass, metal and wood, as well as other solid and liquid substances not normally found or desirable in a properly functioning body cavity. Under normal conditions, these cavities are essentially selfcleaning, being constantly cleaned by a system of scavenger cells and macrophages and constant flushing by freshly manufactured aqueous fluids.

The presence of foreign substances in tissue or organ cavities due to invasion, infection, deterioration, age or break down of the self-cleaning system can have symptomatic and pathological ramifications. For example, in the eye, the presence of foreign substances can produce clouding in the intraocular cavity, causing blurred or cloudy vision. In addition, the presence of foreign substances in large enough quantities can cause scarring, production of fibrous tissue membrane and mass, tumors and infection. In the joint, the presence of foreign substances can result in increased friction, inflammation and pain. Generally, the end result is mal- or dysfunction of the tissue or organ cavity.

The visual process and smooth movement of the joints, in particular, each requires a clean, clear environment, free of anatomic distortions secondary to inflammatory fibrous scar tissue formation, dislocated tissues and foreign bodies. Many surgical and medical procedures are presently available to prevent or alleviate cavity dysfunction due to foreign substance build-up by anatomically reconstructing and cleaning cavity spaces after they have been destroyed or are in a state of dysfunction as a result of some pathologic event. However, surgery itself has pathological consequences. Surgical procedures, including those that minimize cavity invasion using fiber optics and microsurgical tools, inevitably involve cutting and manipulating, resulting in the release of tissue, sera and cellular debris. Accordingly, a primary goal in the surgical management of any tissue or organ cavity is the meticulous cleansing of the cavity space of foreign substances to effect and ensure speedy recovery and prompt return of a normal functioning cavity In conventional surgical procedures, even delicate microsurgical procedures, it is virtually impossible to identify and remove all foreign substances from the cavity and cavity surfaces. Moreover, the more involved and complicated the surgical procedures, the greater the amounts of residual tissue, sera and cellular debris created within the cavity space and on tissue surfaces Without effective removal, healing time will be longer and complete recovery will be more difficult.

Conventional debridement or cleansing of body cavities during and following surgery comprises flushing the cavity with biological fluids, such as sterile saline solutions, and mechanical removal. Such debridement does not completely remove all foreign substances and is highly ineffective in removing water soluble and very small foreign substances.

In view of the deficiencies of the prior art, it would be desirable to have a method for the debridement of mammalian bodily cavities which is safe, relatively simple and highly effective in removing foreign substances.

BRIEF SUMMARY OF THE INVENTION

According to the present invention, a method for removing foreign substances from a mammalian cavity containing an aqueous phase comprises injecting into the cavity a water-immiscible, optically clear, biocompatible debridement fluid in an amount sufficient to replace or at least partially displace the aqueous phase, and removing the aqueous phase and the foreign substances from the cavity, or repositioning desirably retained materials (such as an intraocular lens in the ocular cavity), by pushing with the surface of the fluid.

In addition, the present invention is directed to a method for visualizing a transparent foreign substance in a mammalian body cavity comprising injecting into the cavity a water-immiscible, optically clear, biocompatible fluid having a refractive index sufficiently different from that of the foreign substance to cause visible refraction at the interface between the foreign substance and the biocompatible fluid, the fluid being injected in an amount sufficient to at least partially surround the foreign substance, introducing visible light into the cavity, and visualizing the foreign substance as an outline formed at the interface between the fluid and the transparent foreign substance.

Further according to the present invention, a method is provided for removing foreign substances from tissue within a mammalian body cavity wherein the foreign substances form a layer positioned in overlying relation to the tissue, comprising injecting into the cavity a water-immiscible, biocompatible fluid having a specific gravity greater than water and the tissue, the fluid being injected in an amount sufficient to cover the tissue, and mechanically pulling the foreign substances away from the tissue.

The methods of the present invention are preferably performed using perfluorocarbon liquids as the water-immiscible, biocompatible fluids.

BRIEF DESCRIPTION OF THE DRAWINGS

The foregoing summary of the invention, as well as the following detailed description of preferred embodiments, will be better understood when read in conjunction with the appended drawings. For the purpose of illustrating the invention, there are shown in the drawings embodiments which are presently preferred, it being understood, however, that the invention is not limited to the specific arrangements and instrumentalities disclosed. In the drawings:

FIG. 2a is a generalized, schematic cross-sectional view of a human eye illustrating a first embodiment of the method of the present invention;

FIG. 2b is a generalized, schematic cross-sectional view of a human eye illustrating a later stage of the embodiment illustrated in FIG. 2a;

FIG. 3b is a generalized, schematic cross-sectional view of a human eye illustrating a later stage of the embodiment illustrated in FIG. 3a;

FIG. 4b is a generalized, schematic cross-sectional view of a human eye illustrating a third embodiment of the present invention for removing subretinal debris as shown in FIG. 4a;

DETAILED DESCRIPTION OF PREFERRED EMBODIMENTS

Figure 1:
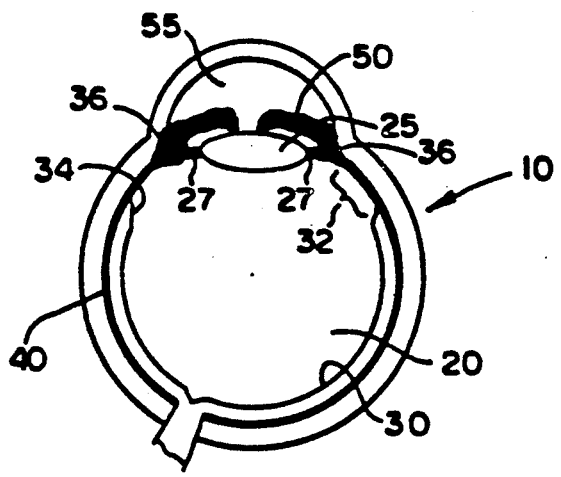
FIG. 1 is a generalized, schematic cross-sectional view of a human eye identifying the major components thereof.

Referring to the drawings, wherein the numerals indicate like elements throughout, there are shown in FIGS. 2 through 6 preferred applications of the present invention. Although the methods of the present invention apply to the debridement of body cavities generally, methods are described and exemplified below with specific reference to the debridement of the intraocular cavity. It will be readily appreciated and understood by one skilled in the medical arts in view of this disclosure, however, how the methods exemplified below may be adapted for use in the debridement of other body cavities, as well as in other types of debridement of the intraocular cavity.

According to the present invention, methods for the debridement of cavities in the mammalian body comprise the intraoperative use of a biocompatible debridement fluid. While not wishing to be bound by any particular theory, the inventor notes that most undesirable foreign substances in body cavities are generally miscible in water or show an affinity for aqueous fluids. Accordingly, the debridement fluid should be water-immiscible so that the foreign substance-containing water phase is distinct from and is displaced by the water-immiscible debridement fluid.

Preferably, the water-immiscible fluid is optically clear, although the liquid could have a color or have a color added using appropriate dyes as desired. The fluid should be optically clear so that the surgeon may visualize the foreign substances desired to be removed from the bodily cavity and may observe the debridement process itself. In addition, it is preferred that the debridement fluid have a low viscosity for ease of insertion and removal of the fluid into and from the body cavity. It is also presently preferred that the debridement fluid be heavier than water so that the foreign substance-containing aqueous phase can be floated out of a closed cavity. This is particularly preferred in those surgical procedures where the position of the patient places the particular body cavity in a position where the bottom (lowermost point) of the cavity is relatively inaccessible to surgical apparatus. The eye of a human patient in a supine position is one example. In cavities where it may be desired to drain foreign substance-containing aqueous phase from the lower or bottom end of the cavity, a debridement fluid lighter than water may be desired.

The presently preferred debridement fluid comprises perfluorocarbon liquids (also called liquid perfluorocarbons). Accordingly, the remainder of this description will be in terms of perfluorocarbon liquids as the debridement fluid. It will be understood, however, that the methods described may be carried out with other debridement fluids having the desired properties discussed above, such as silicone fluids which, although lighter than water, are water-immiscible, optically clear, have low viscosities and are biocompatible.

Many perfluorocarbon liquids are known and described in, for example, U.S. Pat. No. 4,490,351 of Clark, Jr. Perfluorocarbon liquids are generally biocompatible and have been used widely as blood substitutes because of the ability to dissolve substantially more oxygen and carbon dioxide therein than water or other aqueous phases. It is presently believed that virtually any perfluorocarbon liquid may be used to debride bodily cavities in accordance with the present invention. Table 1 contains the physical and chemical characteristics of thirteen perfluorocarbon liquids which are suitable for use in accordance with some or all of the embodiments of the present invention. The physical and chemical characteristics of water are also included in Table 1 for comparison. The thirteen samples, in order with reference to Table 1, include:

1. Perfluoropentane ($C_5F_{12}$),
2. Perfluorodimethylcyclobutane ($C_6F_{12}$),
3. Perfluoromethylcyclopentane ($C_6F_{12}$),
4. Perfluorohexane ($C_6F_{14}$),
5. Perfluoromethylcyclohexane ($C_7F_{14}$),
6. Perfluoroheptane ($C_7F_{16}$),
7. Perfluorooctane ($C_8F_{18}$),
8. Perfluoro-1,3-dimethylcycloh ($C_8F_{16}$),
9. Perfluorodecalin ($C_{10}F_{18}$),
10. Perfluoro-1-methyldecalin ($C_{11}F_{20}$),
11. Perfluorotributylamine (($C_4F_9)_3N$),
12. Perfluorododecahydrofluorene ($C_{13}F_{22}$) and
13. Perfluorotetra-decahydrophenanthrene ($C_{14}F_{24}$).

The presently preferred perfluorocarbon liquids are perfluorooctane, perfluorodecalin and perfluorotetradecahydrophenanthrene, with the first two of these being most preferred.

TABLE 1

| | \multicolumn{13}{c|}{PHYSICAL AND CHEMICAL CHARACTERISTICS OF PERFLUOROCARBON FLUIDS AT 25° C. (UNLESS OTHER TEMPERATURE STATED)} | |
|---|---|---|---|---|---|---|---|---|---|---|---|---|---|---|
| | 1 | 2 | 3 | 4 | 5 | 6 | 7 | 8 | 9 | 10 | 11 | 12 | 13 | WATER |
| Boiling point, °C. | 29 | 45 | 48 | 57 | 76 | 80 | 101 | 102 | 142 | 155 | 174 | 194 | 215 | 100 |
| Distillation range (90% min. distilled), °C. | 28–32 | | | 50–60 | 73–78 | 75–90 | 99–107 | 92–104 | 135–143 | | 165–185 | | | |
| Freezing point, °C. | −120 | −32 | −70 | −90 | −30 | −95 | −65 | −70 | −8 | −70 | −50 | −40 | −20 | 0 |
| Molecular weight | 288 | 300 | 300 | 338 | 350 | 388 | 438 | 400 | 462 | 512 | 671 | 574 | 624 | 18 |
| Specific gravity | 1.604 | 1.6718 | 1.682 | 1.682 | 1.788 | 1.73 | 1.77 | 1.828 | 1.917 | 1.972 | 1.88 | 1.984 | 2.03 | 1 |
| Kinematic viscosity, cSt | 0.29 | 0.59 | 0.615 | 0.39 | 0.87 | 0.55 | 0.8 | 1.06 | 2.66 | 3.25 | 2.8 | 4.84 | 14 | 0.9 |
| Surface tension, mN/m | 9.4 | 11.6 | 12.6 | 12 | 15.4 | 13 | 14 | 16.6 | 17.6 | 18.5 | 16 | 19.7 | 19 | 72 |
| Refractive index | 1.2383 | 1.2555 | 1.265 | 1.2509 | 1.2781 | 1.261 | 1.271 | 1.2895 | 1.313 | 1.3195 | 1.291 | 1.3289 | 1.3348 | 1.333 |
| Vapour pressure, mbar | 862 | 505 | 368 | 300 | 141 | 105 | 39 | 48 | 8.8 | 2.9 | 1.7 | <1 | <1 | 31.6 |
| Heat of vaporization at boiling point, kJ/kg | 90.8 | 84.9 | 90.5 | 86.7 | 85.9 | 79.4 | 92 | 82.9 | 78.7 | 75.5 | 71.1 | 71 | 68 | 2257 |
| Specific heat, kJ/kg °C. | 1.05 | 1.13 | 0.878 | 1.07 | 0.963 | 1.045 | 1.045 | 0.963 | 1.05 | 1.09 | 1.045 | 0.92 | 1.07 | 4.18 |
| Thermal conductivity, mW/m °C. | 64 | | 66.4 | 60 | 59.9 | 60 | 64 | 60.4 | 57 | 57.5 | 66 | 56 | 52.6 | 586 |
| Critical temperature, °C. | 148.7 | 171.7 | 180.8 | 178 | 212.8 | 205 | 229 | 241.5 | 292 | 313.4 | 294 | 357.2 | 377 | 374 |
| Critical pressure, bar | 20.48 | 21.5 | 22.64 | 18.34 | 20.19 | 17.5 | 16.6 | 18.81 | 17.53 | 16.6 | 11.4 | 16.2 | 14.6 | 221 |
| Critical volume, l/kg | 1.626 | | 1.567 | 1.582 | 1.522 | | | 1.52 | 1.521 | 1.5 | | 1.59 | 1.58 | |
| Coefficient of expansion ml/ml °C. | 0.00189 | | 0.00167 | 0.00159 | 0.00138 | 0.0015 | 0.0014 | 0.00123 | 0.00104 | 0.00097 | 0.0012 | 0.00078 | 0.00075 | 0.0002 |
| Acoustic velocity, m/s | 468 | | | 515 | 578 | 542 | 575 | 609 | 711 | | 655 | 875 | | 1498 |

Those skilled in the art will appreciate, however, in view of the present disclosure that other perfluorocarbon liquids having the desired properties described herein may be used as debridement fluids in accordance with the present invention.

Where the debridement fluid is intended for use in the intraocular or other cavity where it is important that the surgeon visualize the foreign substance or observe the debridement process (discussed below), it is preferred that the perfluorocarbon liquid have a refractive index which differs from the refractive index of the cavity aqueous phase by an amount or degree sufficient to allow visualization of the interface between the aqueous phase and the debridement fluid. As an analogous example, oil is immiscible with water and has a different refractive index. When oil is added to the surface of a water container, the oil does not mix with the water and can be seen to be floating on the top of the water surface. Even when shaken, an emulsion results and individual oil droplets can be visualized by the dark border at the interface of the oil and water due to visible refraction caused by the different refractive indices of the two liquids.

In accordance with the present invention, debridement fluids may be used to clean cavity spaces intraoperatively and, in particular, in conjunction with closed cavity surgery, such as operations on the eye and arthroscopic procedures. One skilled in the art will appreciate in view of this disclosure that many procedures to surgically remove foreign substances from body cavities may be performed using the debridement fluids of the present invention. Further, many known surgical procedures, such as the vitrectomy discussed below, may be supplemented with the use of such debridement fluids to avoid complications resulting from the presence of foreign substances in body cavities after surgery.

For example, debridement in accordance with the present invention may be performed in the intraocular cavity, which during surgery is sealed with the exception of two or three small incisions for surgical apparatus. Vitroretinal surgery, for example, is a widely known procedure used for various eye disorders. One specific vitroretinal procedure is pars plana vitrectomy or the surgical removal of the vitreous of the eye. Referring to FIG. 1, the vitreous is an aqueous phase transparent collagen fiber/hyaluronic acid gel matrix which fills the intraocular or vitreous space cavity 20 of the eye 10. The vitreous is normally optically clear, allowing light passing through the lens 25 to reach the retina 30 without distortion. When the vitreous breaks down or liquefies, removal is sometimes indicated.

During pars plana vitrectomy, as many as three incisions are made in the pars plana in three different quadrants, usually at 10 o'clock, 2 o'clock and in the infratemporal quadrant (relative to the eye positioned in a supine patient). This is schematically illustrated in FIGS. 2a, 2b, 3a, 3b, 4b, 5 and 6, generally. An infusion cannula (not shown) is sewn into the infratemporal incision to keep the eye constantly filled with the aqueous phase liquid usually used for this surgery (e.g., a modified balanced salt solution). The superior incisions are generally used for working instruments, such as fiber optic lights (not shown), blunt-tipped needles for injection (insertion apparatus 100) or aspiration (removal apparatus 120), forceps, scissors and mechanical cutters (not shown). Visualization of the procedure is done through the pupil with an operation microscope. Once removed surgically, small pieces of the vitreous remain as well as serum and cellular debris generated from surgical trauma.

Figures 2A, 2B:
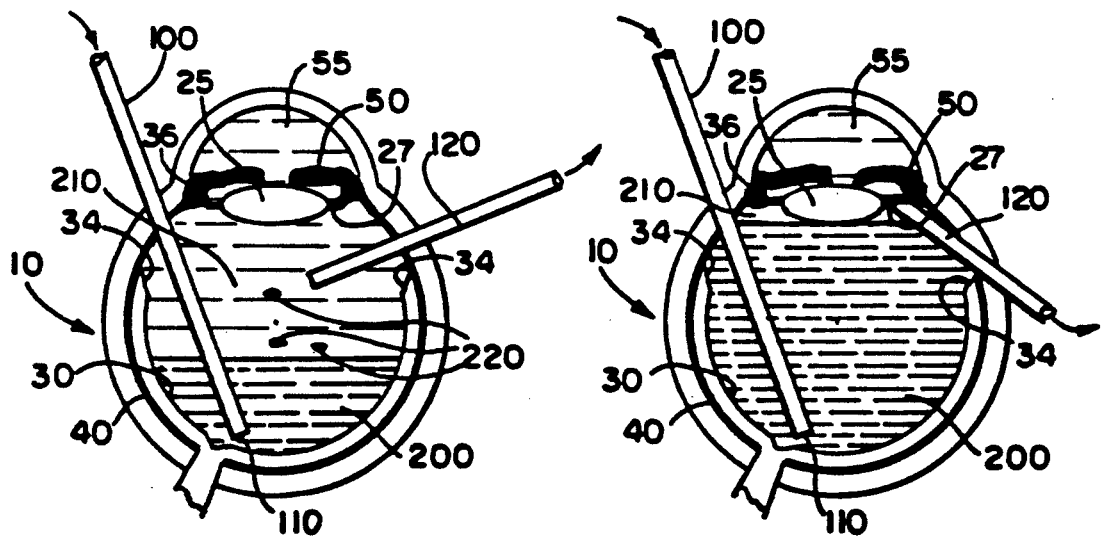

Referring to FIG. 2a, in accordance with the present invention, debridement fluid 200 is introduced into the intraocular cavity of the eye 10 through an incision preferably in the superior region 32 (see FIG. 1) between the front edges 34 of the retina 30 and the ciliary muscles 36 or at a point where insertion apparatus 100, such as a needle-like instrument, may be inserted so that its opening 110 is near a dependent spot in the intraocular cavity, typically just over the retina at the back or lowest point (as shown in the drawings) of the eye (when the patient is lying supine).

The vitreous and any surrounding aqueous phase 210, which are lighter than the debridement fluid (here perfluorocarbon liquid), essentially float on the perfluorocarbon liquid debridement fluid 200. This phenomenon allows the emulsified or liquefied vitreous and the aqueous phase to be conveniently withdrawn from the cavity at a point near the front of the cavity (the top relative to the patient's position) by passive egress through the second superior incision or using suction or removal apparatus 120, such as a foot-activated variable suction pump attached to a blunt-tipped needle.

As the level of the debridement fluid 200 rises in the cavity, the removal apparatus 120 may be repositioned as illustrated, for example, in FIG. 2b for removal of all of the aqueous phase 210 and entrained foreign substances 220. In an aphakic patient (lens removed), the removal apparatus could even extend through the space between the ciliary muscles 36 and zonular fibers 27 where the lens 25 was, through the pupil of the iris 50, and into the anterior chamber 55 to remove aqueous phase and entrained foreign substances from that area of the ocular cavity as well. Simultaneous injection and removal maintains desired cavity pressure and allows for a controlled, measured removal of the aqueous phase and foreign substances.

Debridement fluid is injected into the eye in a preferably slow, controlled, continuous manner to avoid creating an emulsion or fish-egging. An emulsion is generally not desired because complete displacement of the aqueous phase is more difficult to obtain and observe. Especially in pressure sensitive cavities, such as the eye, care should be taken to avoid increasing cavity pressure to a point dangerous to the integrity of cavity tissues or to a point where arterial occlusion may occur.

Debris and other foreign substances may be removed from a body cavity where debridement fluid is injected into the cavity in an amount sufficient to replace or displace and dislodge the aqueous phase foreign substances from the cavity. Where it is desired to rid the cavity of all, randomly located foreign substances, for example, this may require enough debridement fluid to fill the cavity interior. On the other hand, it is not always necessary to completely fill the cavity with debridement fluid. Thus, debridement fluid could partially fill the cavity, and the aqueous phase could be aspirated off the top of the perfluorocarbon liquid (or other heavier than water fluid) on which the aqueous phase is floating. Air or other gas could fill the remainder of the cavity. One skilled in the medical arts will recognize the amount of debridement fluid necessary to remove unwanted aqueous phase and foreign substances in a given debridement procedure in view of this disclosure.

With the cavity completely or partially filled with debridement fluid, the aqueous phase and foreign substances are displaced and removed from the cavity. Any aqueous phase or foreign substances remaining may, where desired, be visualized (discussed below) for mechanical intervention or additional debridement with fresh debridement fluid.

Certain surgical procedures in the eye to repair retinal detachment are performed by filling the intraocular cavity with silicone fluid. In some cases, it becomes necessary to remove the silicone. Silicone fluid is lighter than and immiscible with water and is also immiscible with perfluorocarbon liquids. Accordingly, it is also possible using the methods of the present invention to displace silicone fluid by infusing the intraocular cavity with perfluorocarbon liquid to displace silicone fluid in a manner similar to removal of the liquefied vitreous and aqueous phase discussed above.

Figure 3A:
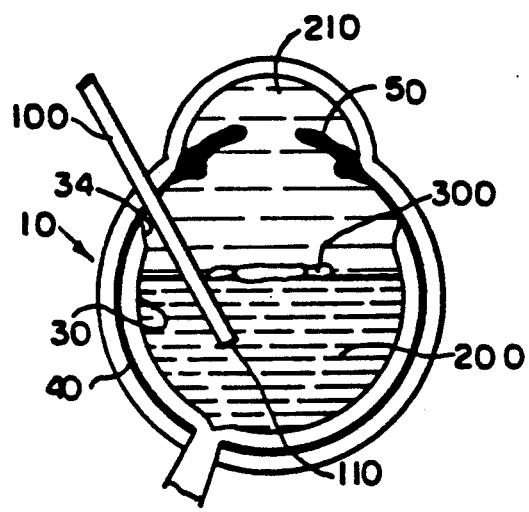
FIG. 3a is a generalized, schematic cross-sectional view of a human eye illustrating a second embodiment of the present invention.
Figure 3B:
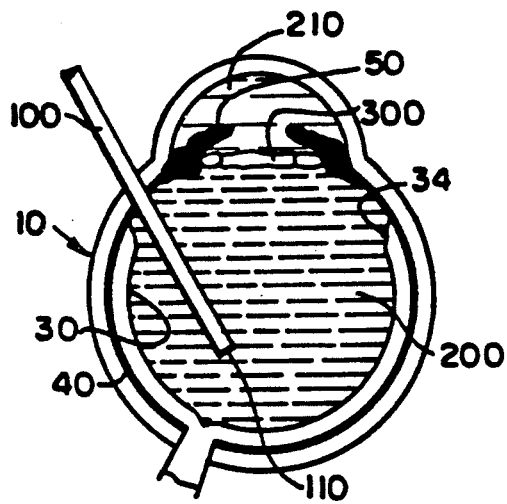

The specific gravity of the debridement fluid of the present invention can also facilitate repositioning or removal of certain ocular bodies. For example, as illustrated in FIGS. 3a and 3b, because intraocular lenses are formed of materials, such as polymethylmathacrylic (PMMA), which float in perfluorocarbon liquids, the infusion of perfluorocarbon liquid into the ocular cavity can be used to float the intraocular lens back into the correct position for suturing or out of the eye in a manner similar to the method for removing other foreign substances discussed generally above. Perfluorocarbon liquid debridement fluid 200 injected into the eye cavity floats an intraocular lens 300 as well as the aqueous phase 210. Using well known surgical tools, the lens 300 is appropriately positioned during perfluorocarbon infusion. As seen in FIG. 3b, when the perfluorocarbon liquid level approaches the desired level, near the iris 50, the intraocular lens 300 may be sutured into position.

Alternatively, the lens may be removed via an incision in the eye (not shown) as desired.

Figure 4A:
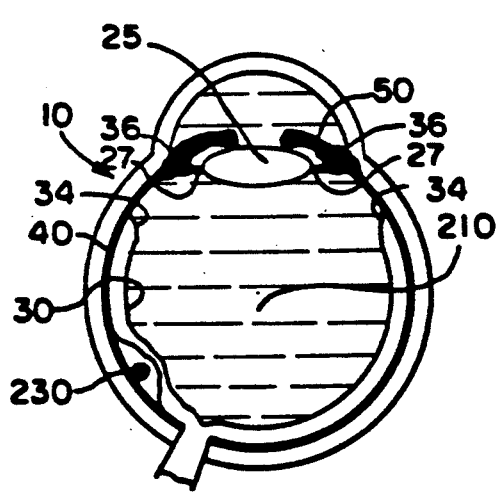
FIG. 4a is a generalized, schematic cross-sectional view of a human eye having sub-retinal debris.
Figure 4B:
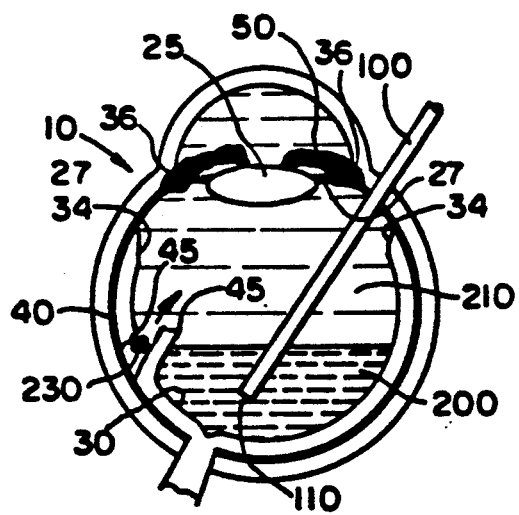

In another embodiment, the debridement fluid may be used in accordance with the present invention to assist in the removal of subretinal pathologic formations, such as hemorrhages, disciform scars, cysts, parasites, larvae, worms, mobile tumors, dislocated cataracts or intraocular lenses and aqueous fluids collected under areas where the retina 30 becomes detached from the choroid 40. As illustrated in FIGS. 4a and 4b, to remove a foreign substance 230 (whether liquid, solid, gas or a combination of these) from behind the retina 30 in accordance with the present invention, perfluorocarbon liquid debridement fluid 200 is injected into the intraocular cavity, preferably near the back (bottom) of the retina and proximate the unwanted foreign substance 230, to displace the debris. Where necessary or desired, a retinal incision 45 may facilitate removal of the foreign substance from behind the retina 30. Normally, however, by means of gravity, the relatively denser perfluorocarbon liquid injected into the intraocular cavity tends to compress the retina, gradually working the foreign substance 230 including any aqueous phase toward the edge 34 of retina 30 as the liquid fills the cavity, thereby facilitating release of any aqueous phase and foreign substance from the subretinal space, and hydraulically urging the retinal layer to return to its proper position for reattachment.

To ensure the complete and effective removal of the aqueous phase, including cellular and fluid debris, in particular small and even microscopic particulate debris and other foreign substances dissolved in the aqueous phase, it may be desired according to another embodiment of the invention to visualize the debridement process. Visualization using debridement fluid in accordance with the present invention may also help facilitate identification and removal of difficult to see foreign substances. Opaque foreign substances present no visualization problems. However, vitreous fragments and other transparent materials may also be identified by infusing the cavity with debridement fluid. Visualization may also be desired to identify and reposition or remove displaced or dislocated intraocular lenses, dislocated cataracts or dislocated nuclear and/or cortical cataract material (a complication generated by phacoemulsification) and other foreign or ocular substances in the posterior cavity of the eye.

Figure 5:
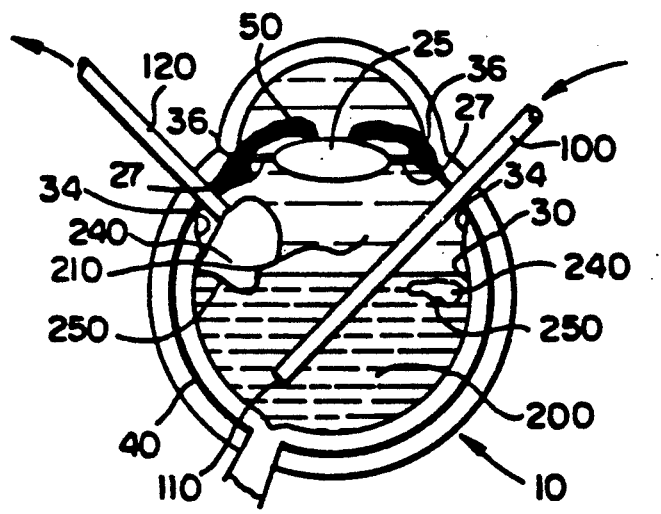
FIG. 5 is a generalized, schematic cross-sectional view of a human eye illustrating a fourth embodiment of the present invention.

Accordingly, referring to FIG. 5, in this embodiment, it is presently preferred to use a debridement fluid 200 which has a refractive index sufficiently different from the refractive index of water to cause visible refraction at the interface or boundary between aqueous phase and/or foreign substance on the one hand and lo the debridement fluid on the other hand. Use of such debridement fluid creates, when subjected to light, a visible boundary (black line or plane) or outline 250 at the interface between the debridement fluid 200 and any aqueous phase or debris 240 remaining in the cavity, due to the differing refractive indices. Identified debris 240 may then be removed by removal apparatus 120, such as a needle or forceps, for example.

Water has a refractive index of 1.333 at 25° C. (see Table 1). Where it is desired to visualize transparent debris and aqueous phase in a bodily cavity, it is presently preferred to use a debridement fluid having a refractive index at least 0.01, and preferably at least 0.02, more or less than water at a given temperature and wavelength of light.

Especially where visualization of the debridement is desired, the debridement fluid must be optically clear, although it may be desired to use a colored debridement fluid, for example, where certain wavelengths of light are being used or where a colored debridement fluid would otherwise aid visualization.

In the intraocular cavity, visualization or observation in accordance with the present invention can be conducted directly through the pupil of the eye or indirectly using commercially available optic means, such as an operating microscope and/or an indirect ophthalmoscope. Fiber optic endoscopes, capable of transmitting and receiving visible light, may also be used. Visualization of an aqueous phase and/or particulate debris/debridement fluid interface boundaries may be aided by internal illumination with a microscope apparatus and/or with a fiber optic scope for removal mechanically or by suction with a fluid removal apparatus.

Figure 6:
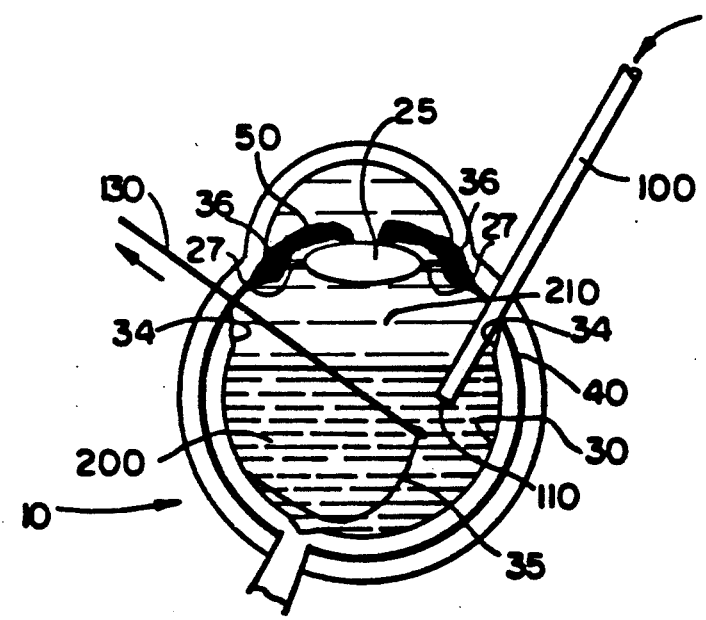
FIG. 6 is a generalized, schematic cross-sectional view of a human eye illustrating a fifth embodiment of the present invention.

In still another embodiment of the present invention illustrated in FIG. 6, debridement fluid is introduced into a closed cavity to apply diffused counter pressure against a first tissue plane when dissecting away foreign substances or another tissue plane overlying the first tissue plane. For example, in the eye, foreign substances or displaced tissue can contact the retina and form a membrane or film 35 thereon which must be removed for proper functioning of the retina 30. Such membranes may be secondary membranes comprising fibrovascular or fibroglial tissue growths, blood clots, or lens capsule, nucleus or cortex, for example. Even careful mechanical removal of the membrane can cause damage to retina in the form of tears as the attached membrane is pulled away.

In accordance with another embodiment of the present invention, perfluorocarbon liquid debridement fluid 200 is introduced into the eye 10 where the patient is positioned so that the retina 30 is beneath the foreign substances or tissue plane 35 to be dissected away. As discussed above, the relatively dense weight of the perfluorocarbon liquid presses downward against the retina 30 as a counter force to the pulling effect of the membrane being pulled away from the retina by dissection apparatus 130. Because the perfluorocarbon liquid is spread out across the retinal layer, downward pressure is spread out across the retina to provide a gentle, uniform counter force against the dissection forces.

Further according to the present invention, perfluorocarbon liquids may be used to protect body cavity cells and tissues from foreign substances. For example, certain ocular surgical procedures permanently replace the vitreous with very pure silicone oil. Normally, very pure silicone oil is not taken up by the cells of the cavity because the molecules are too large. Over time, however, silicone molecules break down and become absorbable by the cavity cells and tissues. Perfluorocarbon liquids also have a large molecular size and cannot be taken up by cavity cells. Unlike silicone, however, perfluorocarbon liquids do not break down over time.

While not wishing to be bound by any particular theory, the inventor believes that when perfluorocarbon liquids are contacted with silicone, a chemical reaction occurs, whereby a molecular layer of perfluorocarbon liquid forms to envelope the silicone. Thus, in accordance with another embodiment of the present invention, silicone molecules can be encapsulated by perfluorocarbon liquids to protect body cells from silicone breakdown by introducing perfluorocarbon liquid into a cavity containing a body of silicone oil.

In still another embodiment of the present invention, the large oxygen and carbon dioxide-carrying capacity of perfluorocarbon liquids makes them useful for treatment of oxygen-starved cavity cells and tissues. For example, in the eye where oxygen is essential to the health and function of the retina, perfluorocarbon liquid introduced into the intraocular cavity for debridement purposes may also be used to supply oxygen to retinal cells starved of oxygen due to various retinal and/or vascular abnormalities. In accordance with the present invention, an oxygen-saturated perfluorocarbon liquid is injected into the intraocular cavity, supplementing or replacing the vitreous.

Oxygen in the perfluorocarbon liquid is available to the eye cavity cells and, similarly, carbon dioxide excreted by cells can be dissolved in the perfluorocarbon liquid. When the oxygen content of the perfluorocarbon liquid is spent, the oxygen can be reestablished by perfusing oxygen into the perfluorocarbon liquid in situ on a regular basis using a cannula, for example, to maintain a desired oxygen concentration level or by replacing the oxygen-spent perfluorocarbon liquid with fresh oxygen-saturated perfluorocarbon liquid until the underlying problem causing oxygen starvation is corrected surgically or by natural healing of the eye.

Once the desired debridement procedure is complete, the debridement fluids of the present invention may be removed from the body cavity by, for example, active aspiration (suction) with simultaneous infusion of another substance, such as an aqueous solution, silicone oil, or a gas, such as air, to refill the cavity. Those skilled in the art will recognize in view of this disclosure that other means and apparatus may be used to remove the debridement fluids or, if desired, the debridement fluids may be left in the cavity for extended periods of time or for future removal.

The present invention may be embodied in other specific forms without departing from the spirit or essential attributes thereof and, accordingly, reference should be made to the appended claims, rather than to the foregoing specification as indicating the scope of the invention.

I claim:

1. A method for removing foreign substances from a mammalian body cavity containing an aqueous phase comprising injecting into the cavity at a location near the lower portion of the cavity a water-immiscible, optically clear, biocompatible debridement fluid having a specific gravity greater than water in an amount sufficient to at least partially displace the aqueous phase, removing the aqueous phase and the foreign substances from the cavity at a location near the upper portion of the cavity and removing the debridement fluid.

2. The method according to claim 1, wherein the debridement fluid is injected in an amount sufficient to displace all of the aqueous phase.

3. The method according to claim 1, wherein the debridement fluid comprises perfluorocarbon liquid.

4. The method according to claim 3, wherein the perfluorocarbon liquid is selected from the group consisting of perfluoropentane, perfluorodimethylcyclobutane, perfluoromethylcyclopentane, perfluorohexane, perfluoromethylcyclohexane, perfluoroheptane, perfluorooctane, perfluoro-1,3-dimethylcyclohexane, perfluorodecalin, perfluoro-1-methyldecalin, perfluorotributylamine, perfluorododecahydrofluorene and perfluorotetra-decahydrophenanthrene.

5. The method according to claim 4, wherein the perfluorocarbon comprises perfluorooctane or perfluorodecalin.

6. The method according to claim 1, wherein the bodily cavity is the abdominal cavity, thoracic cavity, fallopian tube, uterine cavity, intraocular cavity, intra-articular cavity, central nervous system ventricular cavity or dural spaces.

7. The method according to claim 1, wherein the foreign substances comprise foreign cells, inflammatory cells, blood cells, tumor cells, tissue debris, sera, protein, bacteria, virus, fungi, vitreous, silicone oil or foreign bodies.

8. The method according to claim 3, further comprising perfusing the liquid perfluorocarbon with oxygen prior to injection into the cavity.

9. The method according to claim 8, further comprising repeatedly perfusing the perfluorocarbon liquid after injection into the cavity to maintain a predetermined oxygen concentration level.

10. A method for visualizing a transparent foreign substance or aqueous phase in a mammalian body cavity comprising injecting into the cavity a water-immiscible, optically clear, biocompatible fluid having a refractive index sufficiently different from the refractive index of the foreign substance or aqueous phase to cause visible refraction at the interface between the foreign substance or aqueous phase and the biocompatible fluid in an amount sufficient to at least partially surround the foreign substance, introducing visible light into the cavity and visualizing the foreign substance as an outline formed at the interface between the fluid and the transparent foreign substance or aqueous phase.

11. The method according to claim 10, wherein the fluid comprises perfluorocarbon liquid.

12. The method according to claim 11, wherein the perfluorocarbon liquid is selected from the group consisting of perfluoropentane, perfluorodimethylcyclobutane, perfluoromethylcyclopentane, perfluorohexane, perfluoromethylcyclohexane, perfluoroheptane, perfluorooctane, perfluoro-1,3-dimethylcyclohexane, perfluorodecalin, perfluoro-1-methyldecalin, perfluorotributylamine, perfluorododecahydrofluorene and perfluorotetradecahydrophenanthrene.

13. The method according to claim 10, wherein the biocompatible fluid has a refractive index at least 0.01 more or less than water.

14. The method according to claim 10, wherein the body cavity is the abdominal cavity, thoracic cavity, fallopian tube, uterine cavity, intraocular cavity, intra-articular cavity, central nervous system ventricular cavity or dural spaces.

15. A method for removing foreign substances from tissue within a mammalian body cavity where the foreign substances form a layer which overlies the tissue, comprising injecting into the cavity a water-immiscible, biocompatible fluid, having a specific gravity greater than water and the tissue, in an amount sufficient to cover the tissue, and mechanically pulling the foreign substances away from the tissue.

16. The method according to claim 15, wherein the fluid comprises perfluorocarbon liquid.

17. The method according to claim 16, wherein the perfluorocarbon liquid is selected from the group consisting of perfluoropentane, perfluorodimethylcyclobutane, perfluoromethylcyclopentane, perfluorohexane, perfluoromethylcyclohexane, perfluoroheptane, perfluorooctane, perfluoro-1,3-dimethylcyclohexane, perfluorodecalin, perfluoro-1-methyldecalin, perfluorotributylamine, perfluorododecahydrofluorene and perfluorotetra-decahydrophenanthrene.

18. The method according to claim 15, wherein the tissue comprises the retina.

19. The method according to claim 15, wherein the foreign substances comprise a secondary membrane.

* * * * *